United States Patent
Nishikawa et al.

(10) Patent No.: US 8,465,414 B2
(45) Date of Patent: Jun. 18, 2013

(54) MEDICAL MANIPULATOR DEVICE AND ACTUATOR SUITABLE THEREFOR

(75) Inventors: Atsushi Nishikawa, Suita (JP); Fumio Miyazaki, Suita (JP); Mitsugu Sekimoto, Suita (JP); Kazuhiro Taniguchi, Suita (JP); Kohei Kazuhara, Izumi (JP); Takeharu Kobayashi, Izumi (JP); Takaharu Ichihara, Izumi (JP); Naoto Kurashita, Izumi (JP)

(73) Assignees: Osaka University (JP); Daiken Iki Kabushiki Kaisha (JP)

( * ) Notice: Subject to any disclaimer, the term of this patent is extended or adjusted under 35 U.S.C. 154(b) by 805 days.

(21) Appl. No.: 12/593,700

(22) PCT Filed: Mar. 28, 2008

(86) PCT No.: PCT/JP2008/056194
§ 371 (c)(1),
(2), (4) Date: Feb. 5, 2010

(87) PCT Pub. No.: WO2008/120753
PCT Pub. Date: Oct. 9, 2008

(65) Prior Publication Data
US 2010/0137680 A1 Jun. 3, 2010

(30) Foreign Application Priority Data
Mar. 30, 2007 (JP) ................................ 2007-094181

(51) Int. Cl.
*A61B 1/00* (2006.01)
(52) U.S. Cl.
USPC ............ 600/102; 600/104; 600/107; 600/114

(58) Field of Classification Search
USPC .......................... 600/102, 104, 106, 107, 114
See application file for complete search history.

(56) References Cited

U.S. PATENT DOCUMENTS

| | | | |
|---|---|---|---|
| 6,330,837 B1 * | 12/2001 | Charles et al. | ............. 74/490.06 |
| 7,104,998 B2 | 9/2006 | Yoon et al. | |
| 2003/0004516 A1 | 1/2003 | Yoon et al. | |
| 2004/0133078 A1 * | 7/2004 | Edoga et al. | .................. 600/227 |
| 2006/0001740 A1 | 1/2006 | Fujie et al. | |
| 2006/0100501 A1 | 5/2006 | Berkelman et al. | |
| 2007/0058035 A9 | 3/2007 | Fujie et al. | |

FOREIGN PATENT DOCUMENTS

| | | |
|---|---|---|
| EP | 1 568 445 | 8/2005 |
| JP | 3-292879 | 12/1991 |
| JP | 4210040 | 7/1992 |
| JP | 9-276289 | 10/1997 |
| JP | 10-193030 | 7/1998 |

(Continued)

*Primary Examiner* — Rochelle-Ann J Blackman
(74) *Attorney, Agent, or Firm* — Gerald E. Hespos; Michael J. Porco; Matthew T. Hespos

(57) ABSTRACT

A clean and inexpensive medical manipulator device can be provided in which a risk of failure caused by current leakage or disconnection is eliminated and reliability is higher than in a manipulator device using an electrically driven actuator or electric motor. The medical manipulator device includes a stage section 3 that can hold a medical instrument 2; a plurality of actuators 4 each linked at one end to the stage section 3; and a base section 5 linked to the other end of each of the plurality of actuators 4 and serving as a base for the plurality of actuators 4, wherein each of the actuators 4 causes the medical instrument 2 and the stage section 3 to displace with respect to the base section 5 by extending or contracting in the longitudinal direction of the actuator 4 in response to a pressure of a liquid 6.

22 Claims, 12 Drawing Sheets

FOREIGN PATENT DOCUMENTS

| | | |
|---|---|---|
| JP | 2002-527226 | 8/2002 |
| JP | 2003-24338 | 1/2003 |
| JP | 2003-93403 | 4/2003 |
| JP | 2004129956 | 4/2004 |
| JP | 2005-103048 | 4/2005 |
| JP | 2006336693 | 12/2006 |
| WO | WO 00/21684 | 4/2000 |
| WO | 00/30557 | 6/2000 |

* cited by examiner

MEDICAL MANIPULATOR DEVICE AND ACTUATOR SUITABLE THEREFOR

BACKGROUND OF THE INVENTION

1. Field of the Invention

The present invention relates to a medical manipulator device that displaceably holds a medical instrument.

2. Description of the Related Art

Laparoscopic surgery using a laparoscope and fine thin forceps has been widely used in recent years. FIG. 12 is an explanatory drawing illustrating schematically the laparoscopic surgery using a laparoscope 102 and fine thin forceps 103. As shown in FIG. 12, in laparoscopic surgery, a surgical operation is performed by inserting the laparoscope 102 and fine thin forceps 103 into a body of a patient 101 from a small hole opened in the body of the patient 101. The laparoscope 102 is operated by a camera assistant 105, and the surgeon 106 performs the necessary procedure by using forceps 103, while observing an internal body image of the patient 101 picked up by the laparoscope 102 and projected on the monitor 104. Such laparoscopic surgery became very popular in recent years because its merits include a low physical and mental load on the patient 101.

In the laparoscopic surgery, in order to operate the forceps 103 with both hands, the surgeon 106 usually entrusts the camera assistant 105 with grasping and operating the laparoscope 102. Therefore, where communication between the surgeon 106 and camera assistant 105 is insufficient, a field of view that is optimum for the surgeon 106 cannot be obtained. Further, unstable hands of the camera assistant 105 sometimes destabilize the field of view.

Accordingly, a medical manipulator device such as an endoscopic robot that grasps and positions the laparoscope 102 has been suggested as a replacement for the cameral assistant 105.

For example, Japanese Patent Application Laid-open No. 9-276289 discloses features of a manipulator device that can grasp and position a laparoscope by a spherical joint and link mechanism.

However, with the feathers of the manipulator device disclosed in JP 9-276289 mentioned hereinabove, the entire device is large and the laparoscope is positioned by bending and stretching four links. Therefore, the region occupied by the device when the manipulator device is operated is large. The resultant inconvenience is that the mobility range of the surgeon in the surgery room is restricted.

Further, where an industrial actuator that is used in an industrial robot is to be used in a drive unit of such a medical manipulator device, problems are associated with cleanliness and reliability because the industrial actuators have not been developed for medical applications.

A typical endoscopic robot is equipped with a mechanism using an industrial actuator such as a stepping motor, and cleanliness is ensured, for example, by covering the entire robot with a sterilized drape or keeping the actuator away from the clean field. However, problems associated with reliability of medical manipulator devices using a stepping motor have been indicated. Thus, in a case where such a stepping motor fails during the surgery, it is necessary to interrupt the procedure for a long time in order to discard the robot and switch to the conventional method using no robot.

Further, in a case of industrial actuator with electric drive, failures such as current leakage or disconnection are a source of concern. Limitations are also placed on the cost reduction.

SUMMARY OF THE INVENTION

With the foregoing in view, it is an object of the present invention to provide a medical manipulator device that has higher resistance to failures caused by current leakage or disconnection and higher reliability than electrically driven actuators and motors and also to provide an actuator suitable for such a medical manipulator device.

The medical manipulator device according to one aspect of the present invention that resolves the above-described problems is a medical manipulator device that displaceably holds a medical instrument, including: a stage section that can hold the medical instrument; a plurality of actuators each linked at one end to the stage section; a base section linked to the other end of each of the plurality of actuators; and an introducing chamber which is provided in each of the actuators and into which a liquid can be introduced, wherein each of the actuators causes the medical instrument and the stage section to displace with respect to the base section by extending or contracting in the longitudinal direction of the actuator in response to a pressure of the liquid inside the introducing chamber.

An actuator according to another aspect of the present invention is an actuator for use in a medical manipulator device that holds a medical instrument and comprises a base section and a stage section that can hold the medical instrument, the actuator comprising: a first linking section that is provided at one end of the actuator and can be linked to the base section; a second linking section that is provided at the other end of the actuator and can be linked to the stage section; and an introducing chamber into which a liquid can be introduced, and wherein the actuator extends or contracts in response to a pressure of the liquid introduced into the introducing chamber, so that the first linking section and the second linking section approach or separate from each other.

The present invention can provide a highly reliable medical manipulator device and an actuator suitable therefore.

DETAILED DESCRIPTION OF THE PREFERRED EMBODIMENTS

The preferred embodiment of the present invention will be described below in greater detail with reference to the appended drawings. The below-described embodiment is a specific example of the present invention and places no limitation on the technical scope of the present invention.

Figure 1:
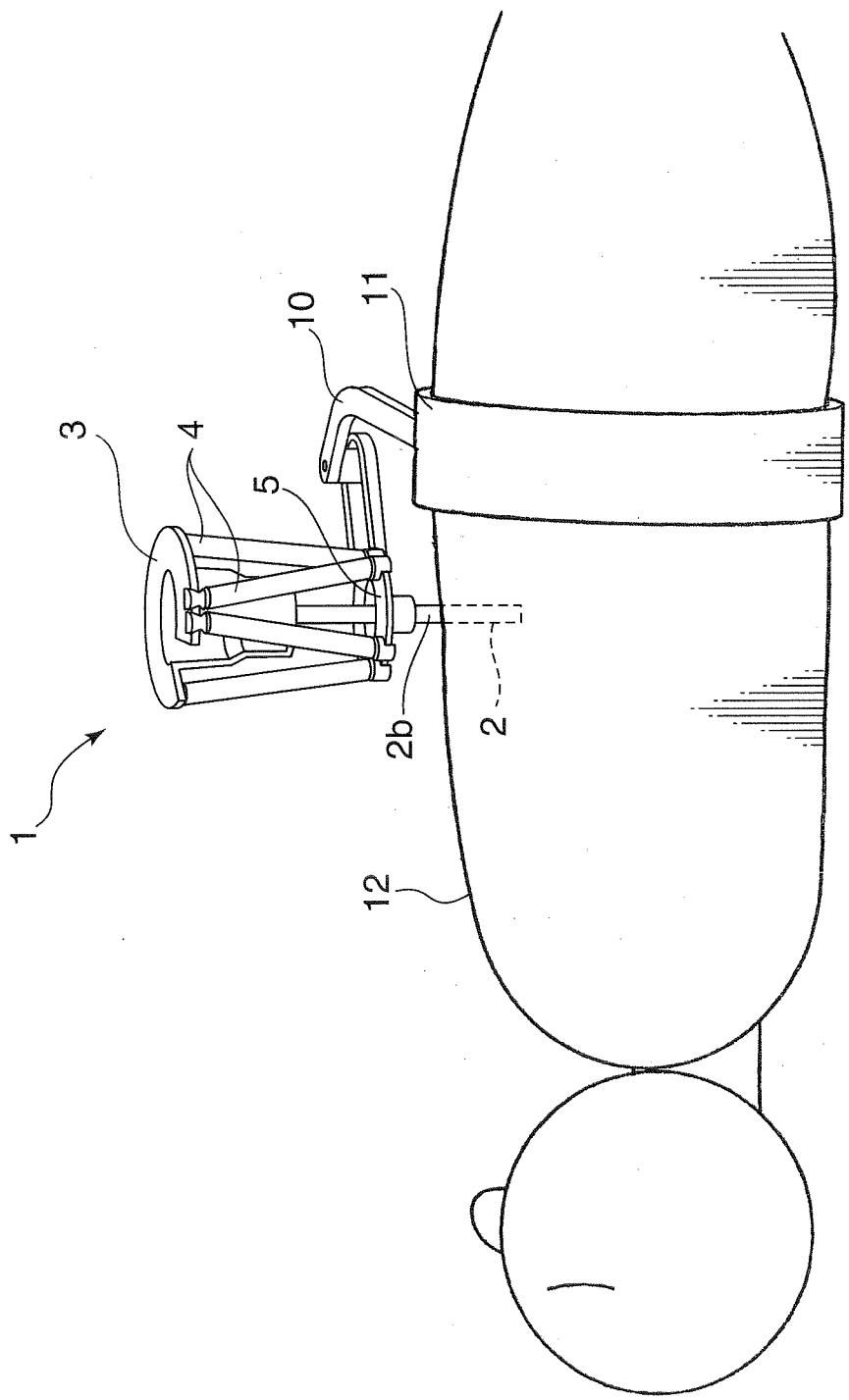
FIG. 1 is an explanatory drawing illustrating the configuration of the medical manipulator device of an embodiment of the present invention.
Figure 2:
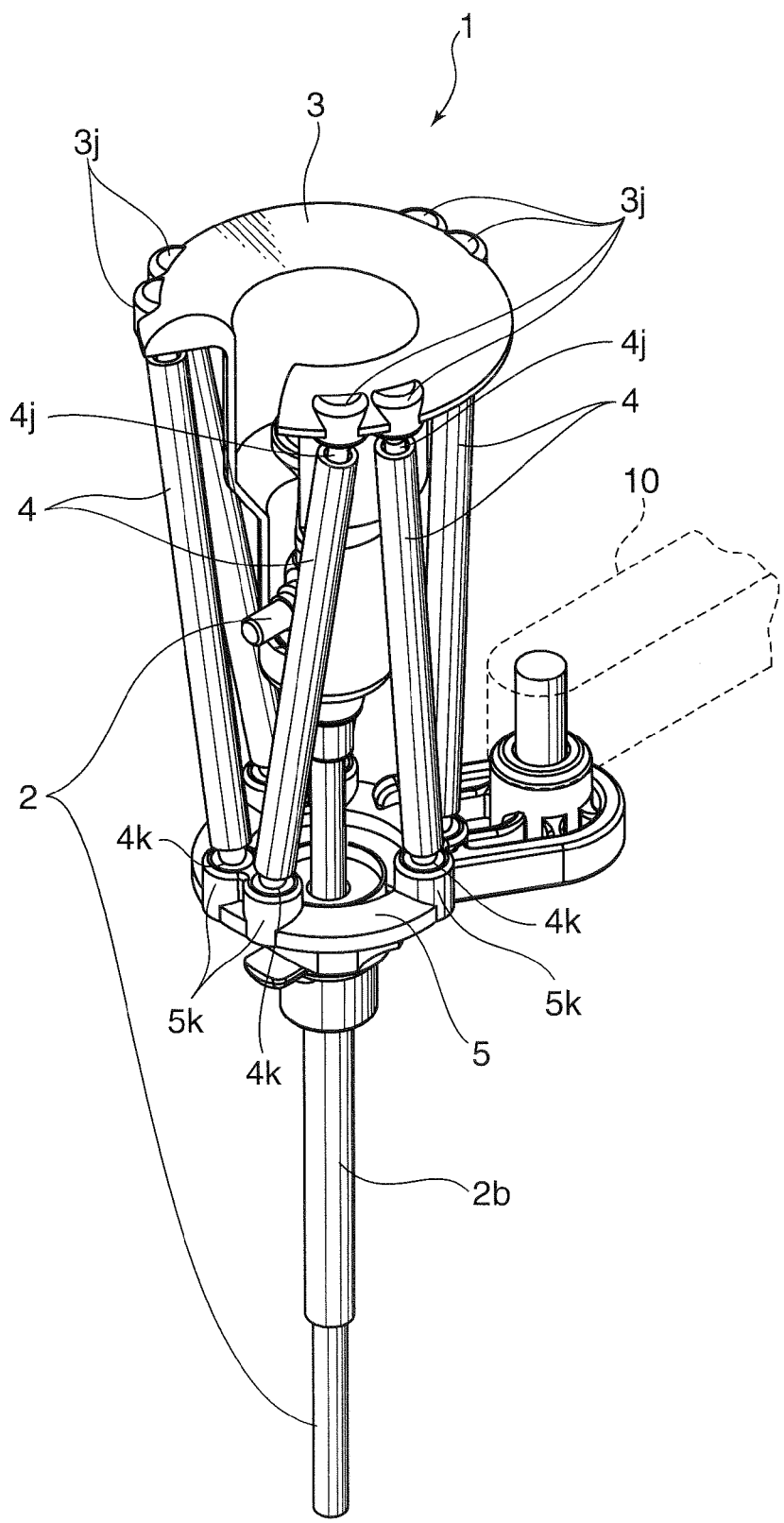
FIG. 2 is a perspective view illustrating the configuration of the medical manipulator device.
Figure 3:
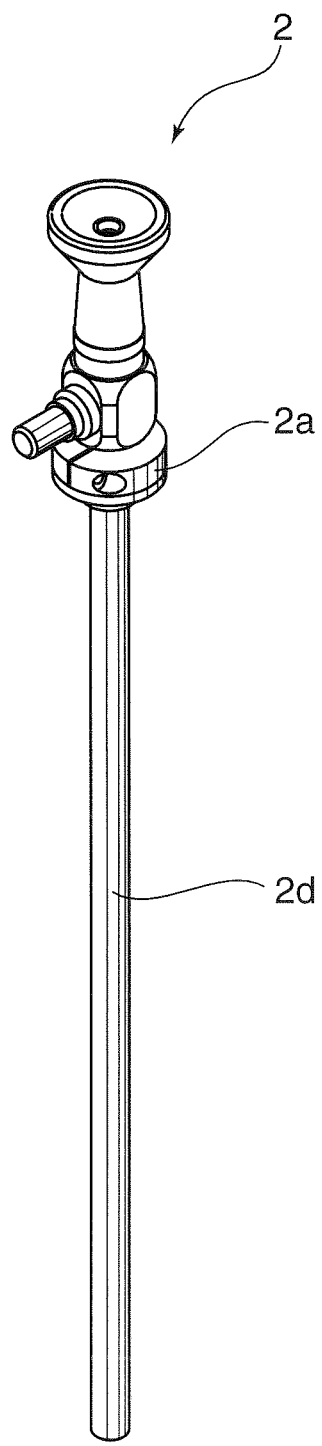
FIG. 3 is a perspective view illustrating the configuration of the medical instrument.
Figure 4:
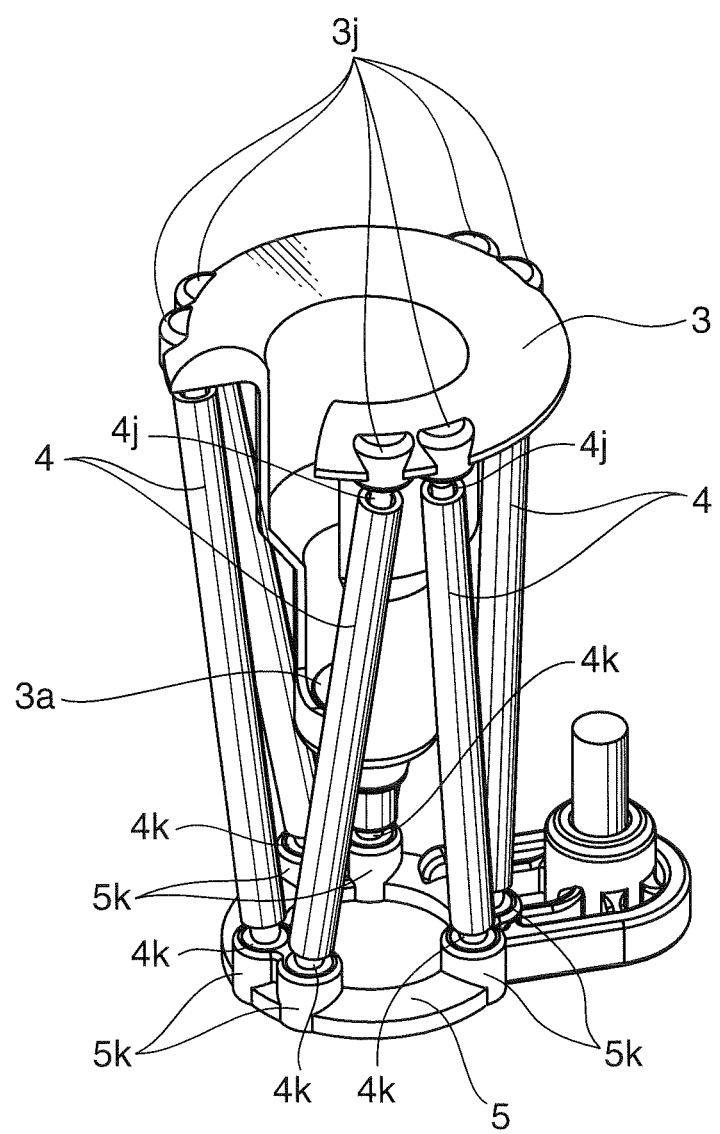
FIG. 4 is a perspective view illustrating the configuration of the medical manipulator device in a state with removed medical instrument.
Figure 5:
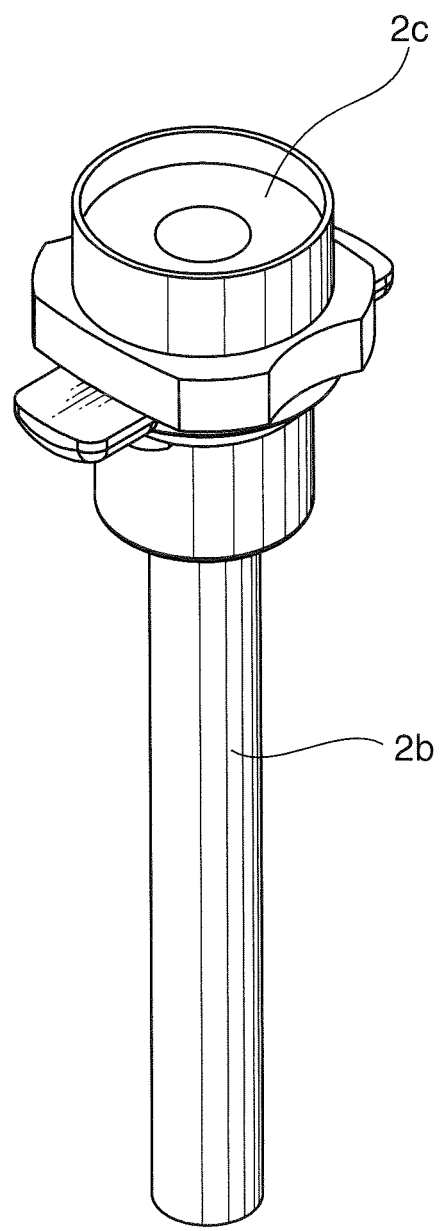
FIG. 5 is a perspective view illustrating the configuration of an attachment aid tool that attaches the lower end of the medical instrument to the medical manipulator device.

FIG. 1 is an explanatory drawing illustrating the configuration of the medical manipulator device 1 of an embodiment of the present invention. FIG. 2 is a perspective view illustrating the configuration of the medical manipulator device 1. FIG. 3 is a perspective view illustrating the configuration of a medical instrument 2. FIG. 4 is a perspective view illustrating the configuration of the medical manipulator device 1 in a state with removed medical instrument 2. FIG. 5 is a perspective view illustrating the configuration of an attachment aid tool 1a for attaching the lower end of the medical instrument 2 to the medical manipulator device 1.

Referring to FIGS. 1 to 4, the medical manipulator device 1 of the embodiment of the present invention is a device for displaceably holding the medical instrument 2. More specifically, the medical manipulator device 1 is provided with a stage section 3 that can hold the medical instrument 2, six actuators 4, and a base section 5 that serves as a base for the actuators 4.

The six actuators 4, base section 5, and stage section 3 constitute a Stewart-Gough mechanism, which is a mechanism that simulates a human neck. In other words, the medical manipulator device 1 is configured so that the position and posture of the stage section 3 with respect to the base station 5 can be controlled and the position of the medical instrument 2 can be adjusted by cooperative action of the six actuators 4.

In the present embodiment, the medical instrument 2 is an endoscope such as a laparoscope for conducting observations in an abdominal cavity or a thoracoscope for conducting observations in a thoracic cavity. As shown in FIG. 3, the medical instrument 2 has an attachment portion 2a composed of a magnetic metal, so that it can be magnetically held with respect a permanent magnet 3a (FIG. 4) provided at the stage section 3.

As shown in FIGS. 1, 2 and 5, the medical instrument 2 is inserted into a body of a patient 12 through a trocar 2b that has punctured the peritoneal membrane of the patient 12. The trocar 2b is a cylindrical member into which a rod-shaped portion 2d (see FIG. 3) of the medical device 2 can be inserted. The trocar has a flange section 2c at one end thereof. The end section of the trocar 2b on the side opposite the flange section 2c can be inserted into the body of the patient 12 in a state in which the flange section 2c is disposed outside the body of the patient 12. The rod-shaped portion 2d of the medical instrument provides additional support to the medical instrument 2 by enabling sliding inside the trocar 2b.

As shown in FIG. 4, the stage section 3 is a resin member that is linked to one end of each of a plurality of actuators 4. Further, the stage section 3 is constituted to be capable of holding the medical instrument 2. In other words, the stage section 3 has a recess in the central portion thereof and a through hole (not shown in the figure) formed in the bottom portion of the recess and is formed to have a cylindrical shape such that the rod-shaped portion 2d of the medical instrument 2 can be inserted therein from above. Further, the stage section 3 also has the permanent magnet 3a provided in the bottom portion of the recess and is configured so that the attachment portion 2a of the medical instrument 2 can be magnetically held, as shown in FIG. 2, by the permanent magnet 3a.

The base section 5 is a portion that serves as a base linked to the other end of each of a plurality of actuators 4 and is configured of a resin annular member. A through hole for inserting the lower portion of the medical instrument 2 supported by the stage section 3 is formed in the central portion of the base section 5. The base section 5 is configured to be linkable to a flexible multi-degree-of-freedom grasping arm 10. The multi-degree-of-freedom grasping arm 10 is provided so as to extend from a fixing member 11. As shown in FIG. 1, in the present embodiment, the fixing member 11 is a belt fixed to the patient 12 for attaching the medical manipulator device 1 in the vicinity of a pelvis of hypogastrium of the patient 12.

The multi-degree-of-freedom grasping arm 10 has a mechanical strength that prevents the shape of the grasping arm from changing under the own weight of the medical manipulator device 1 and flexibility that enables free deformation of this shape. One end of the grasping arm is fixed to the fixing member 11 attached to the patient 12, and the other end of the grasping arm is fixed to the base section 5 of the medical manipulator device 1.

Each actuator 4 is actuated in response to a pressure of a liquid and can displace the medical instrument 2 and stage section 3 with respect to the base section 5 by extending and contracting in the longitudinal direction of the actuator 4.

Figure 6:
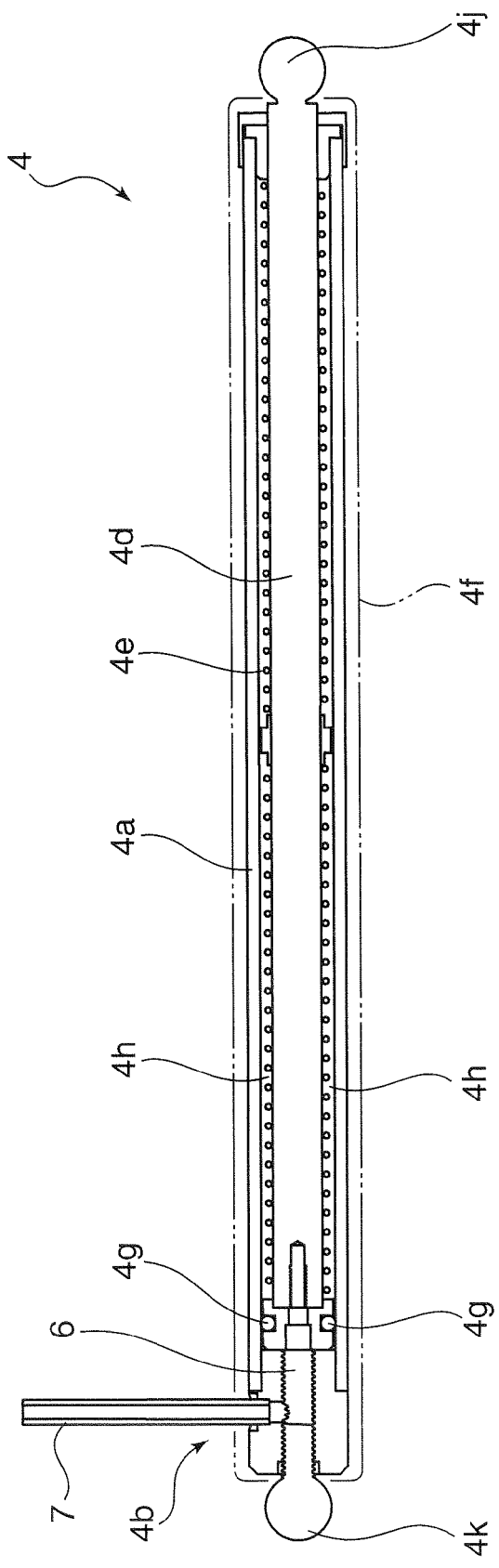
FIG. 6 is a cross-sectional view illustrating the configuration of the actuator.
Figure 7:
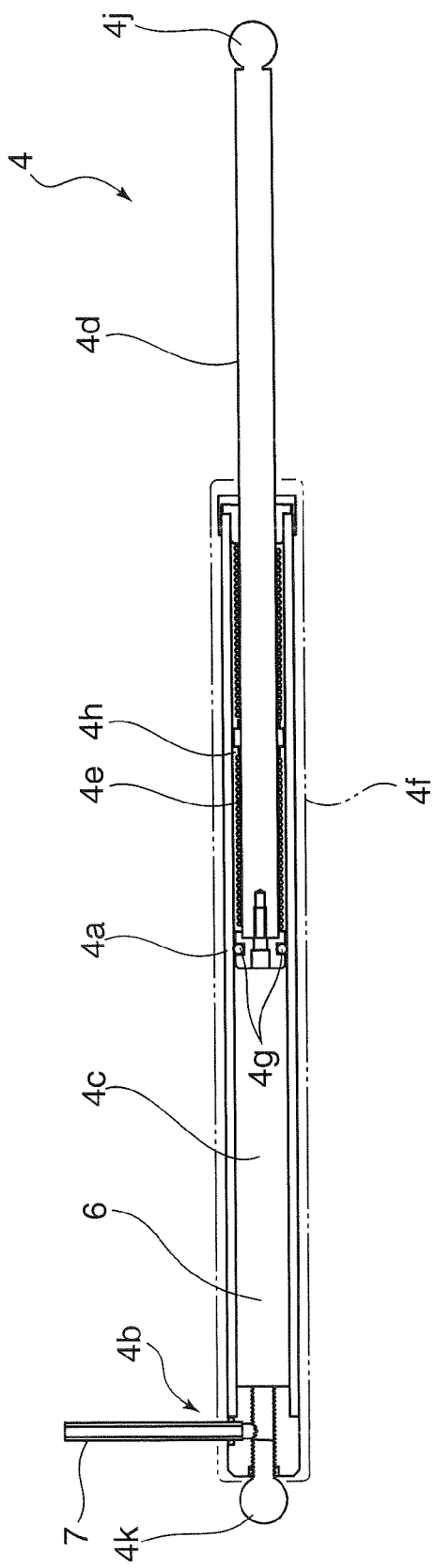
FIG. 7 is a cross-sectional view illustrating a state in which the actuator is extended.
Figure 8:
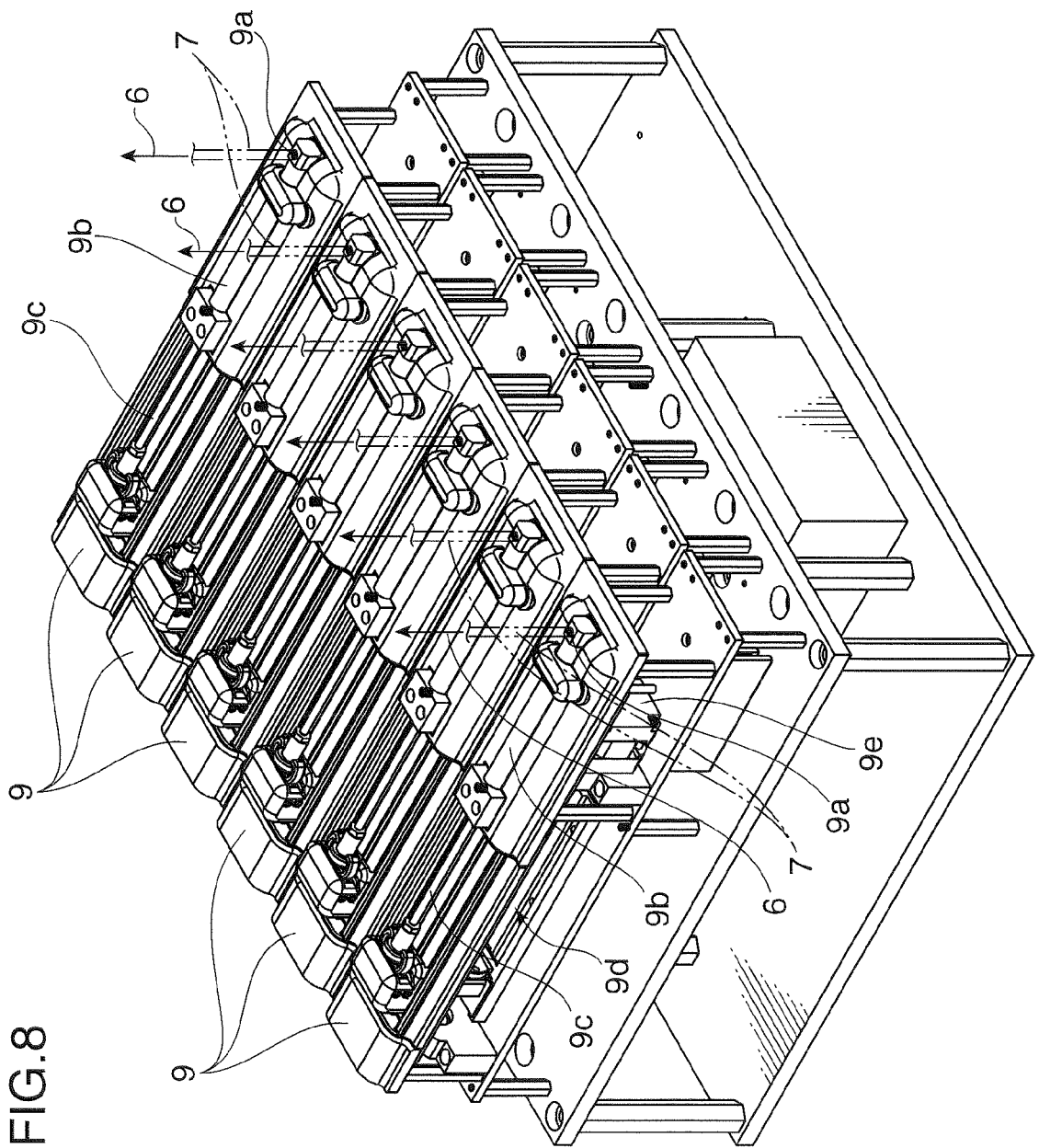
FIG. 8 is a perspective view illustrating a schematic configuration of the pressurized liquid supply device.

FIG. 6 is a cross-sectional view illustrating the configuration of the actuator 4. FIG. 7 is a cross-sectional view illustrating a state in which the actuator 4 is extended. FIG. 8 is a perspective view illustrating a schematic configuration of the pressurized liquid supply device 9.

Referring to FIGS. 6 to 8, each actuator 4 is similar in structure to an injector and includes a cylindrical sleeve 4a that is opened at one end to enable the storage of a liquid 6 that is pressurized water, an inlet/outlet port 4b that is provided in the sleeve 4a and through which the pressurized liquid 6 can be introduced, and a driven member 4d that is provided slidably with respect to an inner wall of the sleeve 4a. As shown in FIG. 7, where the driven member 4d slides inside the sleeve 4a, a storage section 4c (FIG. 7) that can store the pressurized liquid 6 introduced from the inlet/outlet port 4b is formed between the sleeve 4a and driven member 4d.

A lightweight material that excels in impact resistance, heat resistance, and fire resistance such as polycarbonate or aluminum is used to configure the actuator 4. Therefore, the actuator 4 of the present embodiment can be washed and sterilized. For example, the sterilization can include ethylene oxide gas sterilization, autoclave sterilization, and electron beam sterilization. Washing can be ultrasonic washing.

The actuator 4 is also provided with a pushing section 4e between the sleeve 4a and driven member 4d. Because of the pushing section 4e, the driven member 4d constantly applies a force in the direction of contracting the actuator 4 (the direction in which the driven member 4d is inserted into the sleeve 4a).

Furthermore, the actuator 4 is also provided with a coating section 4f composed of a flexible film that covers the outer surface of the actuator 4. The coating section 4f is configured so as to be capable of holding inside thereof the liquid 6 that has leaked from the sleeve 4a. More specifically, the coating section 4f can be configured of a thermally shrinkable tube that covers the sleeve 4a in a state in which the driven member 4d is led out so as to assume a state in which it can extend or contract with respect to the sleeve 4a.

The inlet/outlet port 4b of the actuator 4 is connected to a tube 7 through which the liquid 6 can be introduced.

The tube 7 is connected at one end to the inlet/outlet port 4b and connected at the other end to a pressurized liquid supply device 9 that can supply the liquid 6, as shown in FIG. 8.

Each pressurized liquid supply device 9 is provided with a pressurized liquid supply port 9a connected to the other end of the tube 7, a cylinder 9b, a piston rod 9c that compresses the liquid 6 located in the cylinder 9b, a ball screw mechanism 9d that displaces the piston rod 9c in the longitudinal direction, and a motor 9e that drives the ball screw mechanism 9d.

The pressurized liquid supply port 9a and the tube 7 are connected so that an excess load upon the actuator 4 causes the liquid to leak from the connection site of the pressurized liquid supply port 9a and the tube 7 before the leaks in connection of the liquid inlet/outlet port 4b and the tube 7.

The driven member 4d (FIG. 7) is configured slidably with respect to the inner wall of the sleeve 4a, so as to be displaced to one side in the longitudinal direction of the sleeve 4a in response to a pressure applied to the liquid 6 while maintaining a sealed state with respect to the liquid 6 on the open side of the sleeve 4a.

The driven member 4d of the actuator 4 is provided with a seal mechanism 4g composed of an elastic body in the sliding section between the inner wall of the sleeve 4a and the driven member 4d. The seal mechanism 4g causes the liquid 6 to leak to the open side of the sleeve 4a from a storage section 4c in a state in which an excess load acts upon the actuator 4, thereby conducting sealing in a state in which the pressure of the liquid 6 inside the sleeve 4a can be released. The sleeve 4a has an accumulation section 4h in which the liquid 6 that has leaked from the seal mechanism 4g can be accumulated inside the sleeve 4a.

The pushing section 4e is a stainless steel spring coil that is provided between the sleeve 4a and driven member 4d and elastically biases the driven member 4d toward the inlet/outlet port 4b. In other words, the pushing section 4e is configured to displace the driven member 4d toward the inlet/outlet port 4b in a state in which the pressure of the liquid 6 is reduced.

The linking of the six actuators 4 and stage section 3 is specifically realized by mating an iron spherical shaft 4j (see FIG. 6) that is a magnetic body provided at the actuator 4 and a spherical bearing 3j (see FIG. 4) made from a ferrite magnet-bronze that is a stage-side permanent magnet provided at the stage section 3 and can be magnetically linked to the iron spherical shaft 4j. Because of such a linking, the actuators 4 and the stage section 3 can be magnetically and detachably linked with freedom of angular movement.

The linking of the six actuators 4 and base section 5 is specifically realized by mating an iron spherical shaft 4k (see FIG. 6) that is a magnetic body provided at the actuator 4 and a spherical bearing 5k (see FIG. 4) made from a ferrite magnet-bronze that is a stage-side permanent magnet provided at the base section 5 and can be magnetically linked to the iron spherical shaft 4k. Because of such a linking, the actuators 4 and the base section 5 can be magnetically and detachably linked with freedom of angular movement.

Because the spherical shafts 4j, 4k are thus grasped and fixed only by magnetic forces of the spherical bearings 3j, 5k, the actuators 4 can be easily taken off by hand.

The operation of the medical manipulator device 1 of the embodiment of the present invention will be explained below with reference to FIGS. 1 to 9.

First, the motor 9e drives the ball screw mechanism 9d in the pressurized liquid supply device 9 shown in FIG. 8 and the piston rod 9c is displaced in the longitudinal directions and compresses the liquid 6 located inside the cylinder 9b. As a result, the liquid 6 is introduced from the pressurized liquid supply port 9a into tube 7.

The liquid 6 located inside the tube 7 is pressurized by the liquid 6 introduced from the pressurized liquid supply port 9a, and the liquid 6 is introduced into the sleeve 4a via the tube 7 and inlet/outlet port 4b.

Under the effect of the pressure applied to the liquid 6, the driven member 4d is displaced to one side in the longitudinal direction of the sleeve 4a, while maintaining a sealed state with respect to the liquid 6.

Thus, the actuator 4 moves in the direction of extension because the liquid 6 is introduced from the pressurized liquid supply device 9 into the sleeve 4a via the tube 7.

Where the amount of liquid 6 inside the sleeve 4a decreases, the driven member 4d is displaced toward the inlet/outlet port 4b and the actuator 4 is contracted by the biasing force of the pushing section 4e correspondingly to the reduction in pressure of the liquid 6.

The actuator 4 is provided with the pushing section 4e because where a negative pressure is created inside the sleeve 4a, the volume of gas contained therein increases, thereby slowing the operation of the actuator 4.

Each actuator 4 is thus actuated in response to the pressure of liquid 6 and extends or contracts in the longitudinal direction of the actuator 4, whereby displacing the medical instrument 2 and stage section 3 with respect to the base section 5.

In the medical manipulator device 1, the positioning of the medical instrument 2 can be conducted by controlling the position and posture of the stage section 3 by cooperative action of these six actuators 4. Thus, by using the medical manipulator device 1, it is possible to observe the abdominal cavity or thoracic cavity in a state in which the medical instrument 2 is held displaceably.

Figure 9:
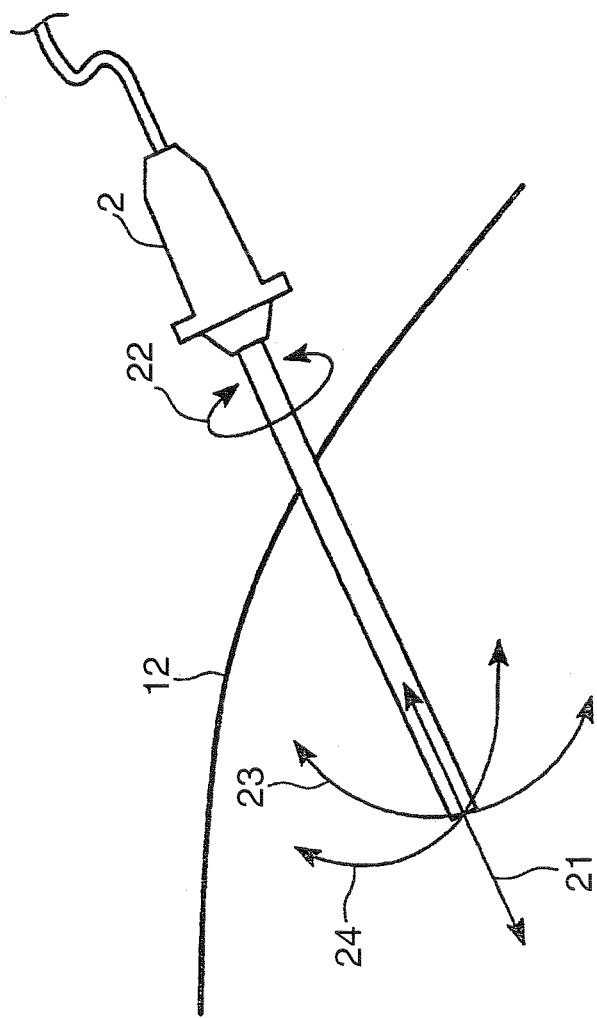
FIG. 9 is an explanatory drawing illustrating the operation of the medical instrument with the medical manipulator device.

FIG. 9 is an explanatory drawing illustrating the operation of the medical instrument 2 with the medical manipulator device 1. As shown in FIG. 9, the medical device 2 held at the stage section 3 can be caused to move with four degrees of freedom: in and out 21, roll 22, pitch 23, and yaw 24.

Because the actuator 4 is linked magnetically and detachably by mating of the spherical shafts 4j, 4k and spherical bearings 3j, 5k, the actuator 4 can be easily taken out by hand.

Where an excess load is applied to the actuator 4, the seal mechanism 4g acts upon the liquid 6 so as to cause the liquid 6 to leak to the open side of the sleeve 4a from the storage section 4c and releases the pressure of liquid 6 located inside the sleeve 4a. In this case, the leaked liquid 6 is accumulated in the accumulation section 4h located inside the sleeve 4a.

The liquid 6 that could be accommodated in the accumulation section 4h and has leaked out from the sleeve 4a is held between the outer surface of the sleeve 4a and the coating section 4f.

Where an even larger load acts upon the actuator 4, the liquid 6 leaks in the connection portion of the pressurized liquid supply port 9a and tube 7 before the liquid 6 leaks in the connection portion of the inlet/outlet port 4b and tube 7.

As described hereinabove, with the medical manipulator device 1 of the present embodiment of the invention, the medical instrument 2 and stage section 3 are displaced with respect to the base section 5 by longitudinal extension or contraction of a plurality of actuators 4 provided between the stage 3 that holds the medical instrument 2 and the base section 5 that serves as a base. Therefore, no significant space is required for operating the medical instrument 2 and it is possible to provide a compact and lightweight manipulator device that occupies a small area during operation.

In particular, because each actuator 4 is actuated and caused to extend or contract by a pressure of liquid 6, for example, by a water pressure drive, each actuator 4 can be manufactured at a lower cost than an electrically driven actuator 4 or electric motor 9e. Further, there is no risk of failure caused by current leakage or disconnection and reliability is high.

Further, because the medical instrument 2 is magnetically held by the stage section 3, the medical instrument 2 can be easily attached to the stage 3 and detached therefrom. As a result, even if either of the medical instrument 2 and actuator 4 fails, the failed unit can be rapidly replaced. Therefore, reliability is high.

Further, because the actuator 4 is magnetically and detachably linked to the stage section 3 and base section 5, the actuator 4 can be easily attached to the stage 3 and base 5 and detached therefrom. As a result, even if the actuator 4 fails, it can be rapidly replaced with another actuator 4. Therefore, reliability is high.

Further, because the actuator 4 alone can be taken off and the entire actuator 4 can be sterilized, the device can be maintained in a clean state.

Such an actuator 4 that operates in response to the pressure of liquid 6 can be manufactured at a low cost. Therefore, the actuator 4 can be made disposable, that is, the actuator can be used as is and can be discarded after one use. As a result, cleanliness and reliability can be uniformly controlled by the manufacturer, thereby making it possible to raise the level of cleanliness and reliability. Moreover, the load of maintenance at the medical site can be also reduced.

With the medical manipulator device 1, the actuators 4 are magnetically and detachably linked to the state section 3 and base section 5 with freedom of angular movement by mating the spherical shafts 4j, 4k composed of a permanent magnet or a magnetic body with the spherical bearings 3j, 5k that can be magnetically linked to the spherical shafts 4j, 4k. Therefore, it is possible to realize the medical manipulator device 1 that has a wide operation range and good attachment and detachment ability of the actuators 4.

Where the pressure of liquid 6 is reduced, the pushing section 4e causes the displacement of the driven member 4d toward the inlet/outlet port 4b. Therefore, even when the volume of gas bubbles in the liquid 6 increases due to pressure reduction and the drive force of the liquid 6 decreases, this decrease can be compensated and the operation of the driven member 4d toward the inlet/outlet port 4b can be ensured.

Further, the medical manipulator device 1 is configured so that where an excess load acts upon the actuator 4, the liquid is caused to leak and the pressure inside the sleeve 4a is released. Therefore, the application of an excess force to the affected area can be prevented. Further, the leaked liquid 6 is accumulated in the accumulation section 4h located inside the sleeve 4a and therefore the liquid 6 is not scattered and reliability is high.

Further, the medical manipulator device 1 is configured so that where an excess load acts upon the actuator 4, the liquid 6 is caused to leak from the connection site of the pressurized liquid supply port 9a and tube 7 and the pressure of liquid 6 inside the sleeve 4a is released. Therefore, not only the application of an excess force to the affected area can be prevented, but also reliability is further increased because the liquid 6 is caused to leak in a location far from the affected area.

Further, because the liquid 6 that has leaked from the actuator 4 is held between the coating section 4f and the outer surface of the actuator 4, the liquid 6 is not scattered and reliability is further increased.

In a case where the actuator 4 is broken, fractured pieces of the actuator 4 can be prevented from scattering.

Further, because the liquid 6 includes either water or silicone oil as a main component, it is possible to realize the actuator 4 that combines steady operation with low cost and high reliability.

Because the Stewart-Gough mechanism is used, fine operation with multiple degrees of freedom can be realized with a large number of actuators 4. Because the operation of the medical manipulator device 1 does not depend on one actuator 4, reliability is high.

With the medical manipulator device 1 of the embodiment of the present invention, it is possible to realize a manipulator device of an endoscope such as a laparoscope or a thoracoscope that is compact, lightweight, inexpensive, and reliable. In the medical manipulator device 1, the base section 5 is provided so as to extend from the fixing member 11 that is fixed to the patient 12. Therefore, even when the patient 12 moves, the manipulator device is also displaced following the movement of the patient 12. As a result, the medical instrument 2 can be operated with good accuracy with respect to the affected area.

Because the medical manipulator device can be attached reliably to the patient 12, the medical instrument 2 can be moved with better accuracy with respect to the affected area.

Thus, it is possible to realize the medical manipulator device 1 of a wearable type that is attached to the body of the patient 12, and even if the posture of the patient 12 changes during the operation, the relative position or posture of the laparoscope with respect to the patient 12 does not change. Therefore, the patient 12 can be prevented from injury and high reliability can be ensured.

In the above-described embodiment, the actuator 4 is explained in which a spring coil is used as the pushing section 4e, but a mechanism for introducing compressed air can be also used as the pushing section.

Figure 10:
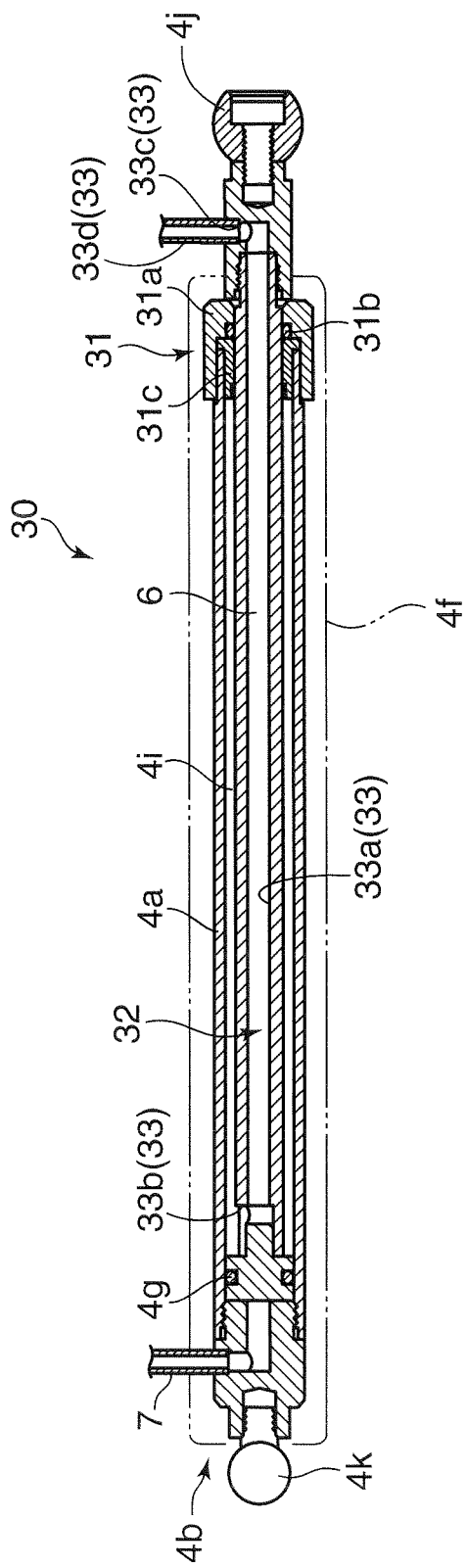
FIG. 10 is a side sectional view illustrating a modification example of the actuator, and showing a state in which the driven member is contracted.
Figure 11:
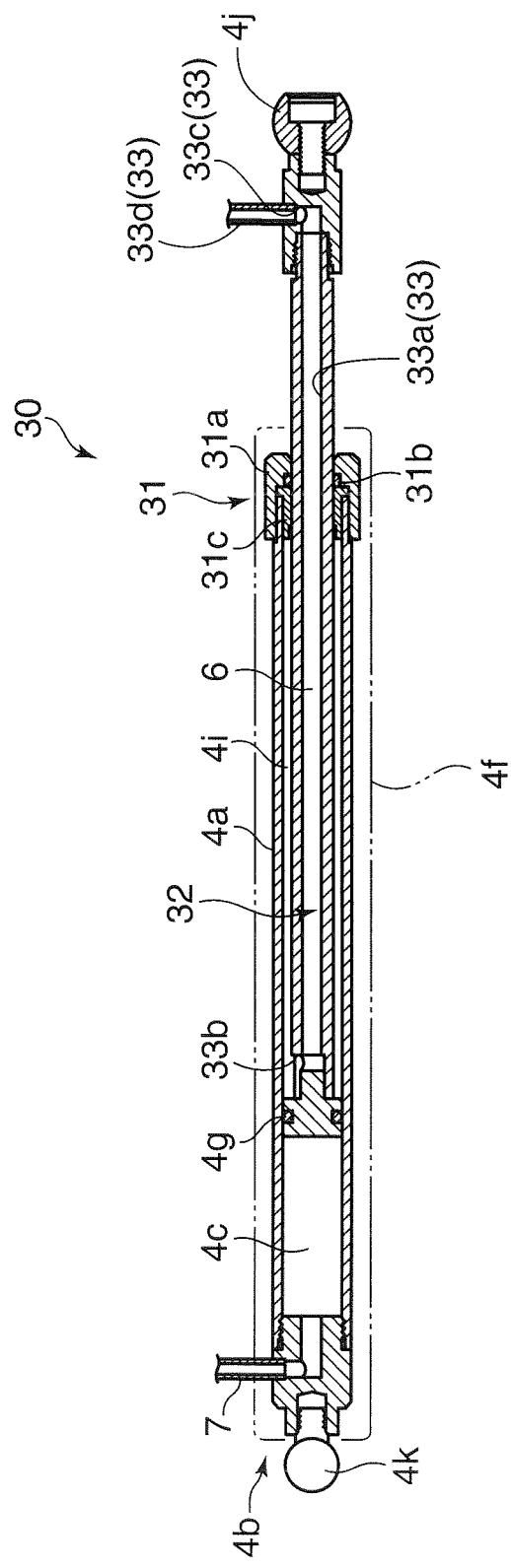
FIG. 11 shows a state in which the driven member in the actuator shown in FIG. 10 is extended.
Figure 12:
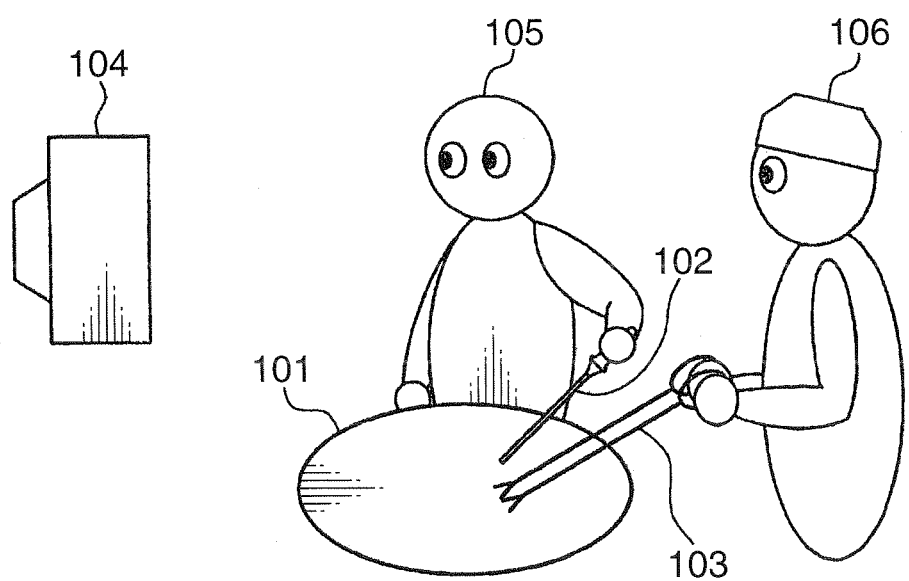
FIG. 12 is an explanatory drawing illustrating schematically laparoscopic surgery using a laparoscope and thin fine forceps.

FIG. 10 is a side sectional view illustrating a modification example of an actuator 30 of an embodiment of the present invention. FIG. 11 is a side sectional view showing a state in which the driven member shown in FIG. 10 is extended. The components similar to those of the actuator 4 of the above-described embodiment are assigned with same reference numerals and explanation thereof is herein omitted.

Referring to FIGS. 10 and 11, the actuator 30 is provided with the sleeve 4a, a lid member 31 that is provided at the open end of the sleeve 4a, and a driven member 32 that is provided slidably with respect to the inner wall of the sleeve 4a.

The lid member 31 is provided with a lid body 31a that covers the open end of the sleeve 4a, a packing 31b that is provided between the lid body 31a and the driven member 32, and a seal material 31c that is fixed to the inner wall of the sleeve 4a.

The lid body 31a is a cylindrical member having formed therein a hole for inserting the driven member 32. The packing 31b is configured to seal the space between the inner wall of the lid body 31a and the outer side surface of the driven member 32, while maintaining a state in which the lid body 31a and driven member 32 can slide.

The seal material 31c is configured to seal the space between the sleeve 4a and the driven member 32, while maintaining a state in which the sleeve 4a and driven member 32 can slide. Because of the seal material 31c, an introducing chamber 4i is formed between the seal material 31 and the seal mechanism 4g inside the sleeve 4a.

The difference between the driven member 32 and the driven member 4d is in that the former has a guide passage 33.

The guide passage 33 includes a main passage 33a formed along the longitudinal direction of the driven member 32, a side hole 33b through which the main passage 33a communicates with the introducing chamber 4i, and opening 33c that opens the main passage 33a in the external position of the sleeve 4a, and the tube 33d linked to the opening 33c.

In the present embodiment, the pressurized liquid supply device 9 (see FIG. 8) is connected to the tube 33d, and a compressed air supply source (not shown in the figure) provided in the hospital is connected to the tube 7.

In other words, the actuator 30 of the present embodiment causes the driven member 32 to extend so as to increase the volume of the accumulation section 4c by introducing the air from the compressed air supply source into the accumulation section 4c via the tube 7. By contrast, the driven member 32 is caused to contract so as to increase the volume of the introducing chamber 4i by introducing the liquid 6 from the pressurized liquid supply device 9 into the introducing chamber 4i via the guide passage 33 in the extended state of the driven member 32.

A regulator (not shown in the figure) is introduced between the compressed air supply source and tube 7. This regulator is used to adjust the pressure of the compressed air introduced into the accumulation chamber 4c so as to maintain a constant pressure at all times.

Thus, with the above-described actuator 30, the base 5 and stage 3 are displaced to separate them from each other in the initial state in which the compressed air is introduced before the supply of the liquid 6 from the pressurized liquid supply device 9 is started. In other words, in the initial state, the length of the portion of the medical instrument 2 that protrudes from the base 5 can be made the shortest. Therefore, where the manipulator device is attached to the patient in this state, the medical instrument 2 can be prevented from unintentional contact with the patient.

With the configuration using compressed air, as in the above-described actuator 30, the extension contraction range of the driven member 32 can be increased by comparison with that of the above-described embodiment in which a spring coil is used.

In other words, in a case where a spring coil is used, the extension-contraction stroke of the driven member is restricted by a minimum size of the spring coil in a contracted state and a spring coil size serving to obtain the minimum necessary biasing force, whereas in the case where compressed air is used, such restrictions are eliminated and a large extension-contraction range of the driven member 32 can be designed. More specifically, where a total length in a contracted state of the actuator 4 using a spring coil and the actuator 30 using compressed air is set to 185 mm, the extension size of the driven member 4d in the actuator 4 is 70 mm, whereas the extension size of the driven member 32 in the actuator 30 can be increased to 112.5 mm.

Further, with the configuration using compressed air, as in the actuator 30, the pushing force acting upon the driven member 32 can be maintained at a constant level at all times by adjusting the pressure of the compressed vacant place and therefore the posture of the medical device 2 can be adjusted with greater precision that in a case of a spring coil in which the biasing force changes correspondingly to the deflection amount.

Further, with the spring coil, only the biasing force that has been designed for the coil itself has to be used as the pushing force of the driven member, whereas in a case where compressed air is used, the pushing force applied to the drive member 32 can be adjusted by adjusting the pressure of the compressed air.

In addition, with the actuator 30, weight can be reduced because the spring coil can be omitted.

The above-described embodiments merely illustrate the preferred specific examples of the present invention, and the present invention is not limited to the above-described embodiments.

For example, the liquid 6 in the actuators 4 is not limited to water. A liquid mainly containing silicone oil can be also used as the liquid 6.

Further, linking of one end of the actuator 4, 30 to the stage section 3 and linking of the other end of the actuator 4, to the base section 5 is not necessarily limited to the configurations shown in the figure. The actuator 4, 30 and the stage section 3 can be linked via a stage-side permanent magnet provided at either or both of one end of the actuator 4, 30 and stage section 3. Likewise, the actuator 4, 30 and the base section 5 can be linked via a base-side permanent magnet provided at either or both of one end of the actuator 4, 30 and base section 5. In this case, the stage section 3 and base section 5 can be magnetically and detachably linked to the actuator 4, 30.

Further, it is also possible to provide a spherical shaft 4j, 4k composed of a permanent magnet or a magnetic body at either the stage section 3 and base section 5, or the actuator 4, and provide the spherical bearing 3j, 5k composed a permanent magnet or a magnetic body that can be magnetically linked to the spherical shaft 4j, 4k at the other of the pair. As a result, the stage section 3 and base section 5 can be magnetically and detachably linked with freedom of angular movement to the actuator 4, 30 by mating the spherical shaft 4j, 4k with the spherical bearing 3j, 5k.

In the above-described embodiments, a medical manipulator device equipped with a laparoscope as the medical instrument 2 is explained. However, the medical instrument 2 that is positioned by the medical manipulator device is not limited to a laparoscope and may be, for example, a thoracoscope that is equipped with a camera for picking up images inside the body of the patient 12 in the same manner as in the laparoscope. Alternatively, the medical instrument may be a functional forceps tool of various kinds that can be used for internal therapy or surgery such as removal of tissue or biopsy.

It is not necessary to use a unique device that has been specifically reduced in size and weight as the medical instrument 2 installed at the medical manipulator device 1, and the devices of general use that have been conventionally employed in laparoscopic surgery can be used without any modification. Further, the configuration of the laparoscope (or thoracoscope) is not particularly limited. For example, a configuration that has been conventionally used, for example, of a type in which a lens system and an illumination fiber are incorporated in a fine tube (optical viewing tube or lens barrel) that will be inserted into the patient 12 and a camera itself contained in a large-diameter portion connected to one end of the fine tube, or of a type in which a small camera is mounted on a distal end of a fine tube that will be inserted into the patient 12.

Further, in the above-described embodiments, a wearable medical manipulator device is explained that is attached to the body of the patient 12. However, the present invention is not limited to the device of this type and relates also to a fixed medical manipulator device that is fixed to the floor of the surgery room in the vicinity of the surgery table, or suspended from the ceiling of the surgery room in the vicinity of the surgery table, or fixed to the surgery table. In a case of a fixed medical manipulator device, where the medical manipulator device 1 is supported by the above-described multi-degree-of-freedom grasping arm 10, initial setting of the position or posture of the medical manipulator device 1 with respect to the patient 12 or resetting during surgery can be freely and easily performed.

It goes without saying that various other design modifications can be made without departing from the scope of the invention defined by the claims.

The above-described specific embodiments mainly include the invention having the below-described features.

The medical manipulator device according to one aspect of the present invention that resolves the above-described problems is a medical manipulator device that displaceably holds a medical instrument, including: a stage section that can hold the medical instrument; a plurality of actuators each linked at one end to the stage section; a base section linked to the other end of each of the plurality of actuators; and an introducing chamber which is provided in each of the actuators and into which a liquid can be introduced, wherein each of the actuators causes the medical instrument and the stage section to displace with respect to the base section by extending or contracting in the longitudinal direction of the actuator in response to a pressure of the liquid inside the introducing chamber.

In accordance with the present invention, the medical instrument and stage section are displaced with respect to the base section by longitudinal extension or contraction of a plurality of actuators provided between the stage section that holds the medical instrument and the base section that serves as a base. Therefore, no grand device is required for operating the medical instrument and it is possible to provide a compact and lightweight manipulator device that occupies a small area during operation.

In particular, because each actuator is actuated and caused to extend or contract by a pressure of liquid, for example, by a water pressure drive, each actuator can be manufactured at a lower cost than an electrically driven actuator or electric motor. Further, there is no risk of failure caused by current leakage or disconnection and reliability is high.

It is preferred that in the medical manipulator device, the stage section be configured to be capable of magnetically holding the medical instrument via a permanent magnet provided at either or both of the stage section and medical instrument.

With such a configuration, because the medical instrument is magnetically held by the stage section, the medical instrument can be easily attached to the stage section and detached therefrom. As a result, even if either of the medical instrument and actuator fails, the failed unit can be rapidly replaced. Therefore, reliability is high.

In the above-described medical manipulator device, it is preferred that at least one of the actuators be magnetically and detachably linked to the stage section via a stage-side permanent magnet provided at either or both of one end of the actuator and the stage section, and magnetically and detachably linked to the base section via a base-side permanent magnet provided at either or both of the other end of the at least one actuator and the base section.

With such a configuration, because the actuator is magnetically and detachably linked to the stage section and base section, the actuator can be easily attached to the stage section and base section and detached therefrom. As a result, even if the actuator fails, it can be rapidly replaced with another actuator. Therefore, reliability is high.

Further, because the actuator alone can be taken off and the entire actuator can be sterilized, the device can be maintained in a clean state.

Such an actuator that operates in response to the pressure of liquid can be manufactured at a low cost. Therefore, the actuator can be made disposable, that is, the actuator can be used as is and can be discarded after one use. As a result, cleanliness and reliability can be uniformly controlled by the manufacturer, thereby making it possible to raise the level of cleanliness and reliability. Moreover, the load of maintenance at the medical site can be also reduced.

In the medical manipulator device, it is preferred that a spherical shaft formed by a permanent magnet or a magnetic body be provided at one of the actuator and the stage section, and a spherical bearing that is formed by a permanent magnet or a magnetic body and that can be magnetically linked to the spherical shaft be provided at the other of the actuator and the stage section; a spherical shaft formed by a permanent magnet or a magnetic body be provided at one of the actuator and the base section, and a spherical bearing that is formed by a permanent magnet or a magnetic body and that can be magnetically linked to the spherical shaft be provided at the other of the actuator and the base section; and the spherical shafts and spherical bearings are magnetically and detachably matched so that the actuator, the stage section and base section are angularly adjustably linked.

With such a configuration linking of the actuators is realized by mating the spherical shafts formed by a permanent magnet or a magnetic body with the spherical bearings that can be magnetically linked to the spherical shafts. Therefore, the actuator, the stage section and base section are angular adjustably and magnetically and detachably linked and it is possible to realize the medical manipulator device that has a wide operation range and good attachment and detachment ability of the actuators.

In the medical manipulator device, it is preferred that at least one actuator from among the plurality of actuators be provided with a cylindrical sleeve; a driven member that is provided slidably with respect to an inner wall of the sleeve, while maintaining a sealed state with respect to the liquid, and can be displaced to one side in the longitudinal direction of the sleeve in response to a pressure applied to the liquid; and a pushing section that can push the driven member to the other side in the longitudinal direction of the sleeve, wherein the introducing chamber is formed between the sleeve and the driven member, and the pushing section displaces the driven member to the other side in the longitudinal direction of the sleeve in a state in which the pressure of the liquid is reduced.

With such a configuration, where the pressure of liquid is reduced, the pushing section causes the displacement of the driven member to the other side in the longitudinal direction of the sleeve. Therefore, even when the volume of gas bubbles in the liquid increases due to pressure reduction and the drive force of the liquid decreases, this decrease can be compensated and the operation of the driven member can be ensured.

More specifically, the pushing section can be formed by a biasing section for applying a biasing force between the sleeve and the driven member.

With such a configuration, the pushing section can be realized by using a biasing section such as a coil spring or an air spring.

Further, the pushing section can include a gas chamber that is formed between the sleeve and the driven member, and an introducing passage through which gas can be introduced into the gas chamber, and the pushing section can be configured so that the driven member is pushed in response to a pressure of the gas introduced into the gas chamber.

With such a configuration, the driven member can be pushed to the other side in the longitudinal direction of the sleeve by introducing the air into the gas chamber. In this case, for example, a compressor provided as part of hospital equipment can be used as the air supply source.

Further, by using a feature of introducing the air, as in the above-described configuration, it is possible to increase the extension-contraction range of the driven member with respect to a case where a biasing member such as a coil spring is used.

In other words, in a case where a biasing member is used, the extension-contraction stroke of the driven member is restricted by a minimum size of the biasing member in a contracted state and a maximum size the biasing member for serving to obtain the minimum necessary biasing force. Whereas, since such restrictions are eliminated in the case of a configuration in which gas is introduced, a large extension-contraction range of the driven member can be designed.

Further, when a biasing member is used, only a biasing force that has been designed therefor has to be used as the pushing force of the driven member, whereas in a case where gas is used, the pushing force of the driven member can be adjusted by adjusting the gas pressure.

In the medical manipulator device, it is preferred that the driven member of the actuator be provided with a seal mechanism formed by an elastic body in a sliding section between the inner wall of the sleeve and the driven member, the seal mechanism conduct sealing in a state in which the pressure of the liquid inside the sleeve can be released by causing the liquid to leak to the open side of the sleeve from a storage section in a state in which an excess load acts upon the actuator, and the sleeve have an accumulation section in which the leaked liquid can be accumulated inside the sleeve.

With such a configuration, in a case where an excess load acts upon the actuator, the pressure inside the sleeve can be released by causing the liquid to leak with the seal mechanism. Therefore, even when the medical instrument comes into contact with the patient's body and cannot be further moved, the application of an excess force to the patient can be prevented. Further, because the leaked liquid accumulates in the accumulation section inside the sleeve, the liquid is prevented from scattering and reliability is high.

In the medical manipulator device, it is preferred that the actuator be further provided with a liquid inlet/outlet port that communicates with the introducing chamber, and a tube that is connected at one end to the liquid inlet/outlet port and connected at the other end to a pressurized liquid supply port through which the liquid can be supplied, wherein the pressurized liquid supply port and the tube are connected so that an excess load acts upon the actuator causes the liquid to leak from the connection site of the pressurized liquid supply port and the tube before the leaks in connection of the liquid inlet/outlet port and the tube.

With such a configuration, in a case where an excess load acts upon the actuator, the pressure of liquid inside the sleeve can be released by causing the liquid to leak from the connection site of the pressurized liquid supply port and the tube. Therefore, even when the medical instrument comes into contact with the patient's body and cannot be further moved, the application of an excess force to the patient can be prevented. Furthermore, because the liquid is caused to leak in a position far from the patient, the reliability is higher than in the case in which the liquid leaks in the medical manipulator device itself.

In the medical manipulator device, it is preferred that the actuator be provided with a coating section formed by a flexible film that covers an outer surface of the sleeve.

With such a configuration, the liquid that has leaked from the sleeve can be held between the coating section and the outer surface of the sleeve. Therefore, the liquid is prevented from scattering and even higher reliability is attained.

Further, in a case where the sleeve is broken, fractured pieces of the sleeve can be prevented from scattering.

In the medical manipulator device, it is preferred that the liquid include either water or silicone oil as a main component.

With such a configuration, because the liquid is used that includes either water or silicone oil as a main component, it is possible to realize the actuator that combines steady operation with low cost and high reliability.

In the medical manipulator device, it is preferred that the plurality of actuators together with the base section and stage section constitute a Stewart-Gough mechanism.

With such a configuration, because the Stewart-Gough mechanism is used, fine operation with multiple degrees of freedom can be realized with a large number of actuators. Further, because the operation of the medical manipulator device does not depend on one actuator, reliability is high.

In the medical manipulator device, it is preferred that the medical instrument be an endoscope.

With such a configuration, it is possible to realize a manipulator device that is compact, lightweight, inexpensive, and reliable.

In the medical manipulator device, it is preferred that the medical instrument be an endoscope such as a laparoscope for conducting observations in an abdominal cavity or a thoracoscope for conducting observations in a thoracic cavity.

With such a configuration, it is possible to realize a manipulator device of an endoscope such as a laparoscope or a thoracoscope that is compact, lightweight, inexpensive, and reliable.

In the medical manipulator device, it is preferred that the base section be configured to be linkable to a multi-degree-of-freedom grasping arm with flexibility that is provided so as to extend from a fixing member that is fixed to a patient.

With such a configuration, because the base section is provided so as to extend from the fixing member that is fixed to the patient, even when the patient moves, the manipulator device is also displaced following the movement of the patient. As a result, the medical instrument can be operated with good accuracy with respect to the affected area.

In the medical manipulator device, it is preferred that the fixing member be a belt for attaching the medical manipulator device in the vicinity of a pelvis of hypogastrium of the patient.

With such a configuration, because the medical manipulator device can be attached reliably to the patient, the medical instrument can be moved with better accuracy with respect to the affected area.

Another aspect of the present invention relates to an actuator for use in a medical manipulator device that holds a medical instrument and comprises a base section, and a stage section that can hold the medical instrument, and the actuator includes: a first linking section that is provided at one end of the actuator and can be linked to the base section; a second linking section that is provided at the other end of the actuator and can be linked to the stage section; and an introducing chamber into which a liquid can be introduced, wherein the actuator extends or contracts in response to a pressure of the liquid introduced into the introducing chamber, so that the first linking section and the second linking section approach or separate from each other.

In accordance with the present invention, extension and contraction proceed correspondingly to the liquid pressure, for example, by a water pressure drive. Therefore, the actuator can be manufactured at a lower cost than an electrically driven actuator or electric motor. Further, there is no risk of failure caused by current leakage or disconnection and a highly reliable actuator can be provided.

Where a medical manipulator device is configured by using a plurality of such actuators, the stage section that holds the medical instrument and the base section serving as a base can be displaced by longitudinal extension or contraction of the actuators. Therefore, the operation of the medical instrument can be realized without using a large device and it is possible to provide a compact and lightweight manipulator device that occupies a small area during operation.

It is preferred that the actuator further include a cylindrical sleeve; a liquid inlet/outlet port that communicates with the introducing chamber; a driven member that is provided slidably with respect to an inner wall of the sleeve, while maintaining a sealed state with respect to the liquid from the liquid inlet/outlet port, and can be displaced to one side in the longitudinal direction of the sleeve in response to a pressure applied to the liquid; and a pushing section that can push the driven member to the other side in the longitudinal direction of the sleeve, wherein the introducing chamber is formed between the sleeve and the driven member, the first linking section is provided at one of the sleeve and the driven member, and the second linking section is provided at the other of the sleeve and the driven member; and the pushing section displaces the driven member to the other side in the longitudinal direction of the sleeve in a state in which the pressure of the liquid is reduced.

With such a configuration, where the pressure of liquid is reduced, the pushing section causes the displacement of the driven member to the other side in the longitudinal direction of the sleeve. Therefore, even when the volume of gas bubbles in the liquid increases due to pressure reduction and the drive force of the liquid decreases, this decrease can be compensated and the operation of the driven member can be ensured.

In the actuator, it is preferred that the base section include a first magnetic section; the stage section include a second magnetic section; the first linking section and the second linking section include magnetic bodies; and the first magnetic section and the first linking section, and the second magnetic section and the second linking section be magnetically and detachably linked, respectively.

With such a configuration, the actuator is magnetically and detachably linked to the stage section and base section. Therefore, the actuator can be easily attached to and detached from the stage section and base section. As a result, even if the actuator fails, it can be rapidly replaced with another actuator. Therefore, reliability is high.

It is preferred that the actuator further include a cylindrical sleeve; a driven member that is provided slidably with respect to an inner wall of the sleeve and can be displaced to one side in the longitudinal direction of the sleeve in response to a pressure of the liquid; and a pushing section that can push the driven member to the other side in the longitudinal direction of the sleeve.

With such a configuration, where the pressure of liquid is reduced, the pushing section causes the displacement of the driven member to the other side in the longitudinal direction of the sleeve. Therefore, even when the volume of gas bubbles in the liquid increases due to pressure reduction and the drive force of the liquid decreases, this decrease can be compensated and the operation of the driven member can be ensured.

More specifically, the pushing section can be configured to include a biasing section for applying a biasing force between the sleeve and the driven member.

With such a configuration, it is possible to realize a pushing section by using a biasing section such as a coil spring and an air spring.

Further, the pushing section can be configured to include: a gas chamber that is formed between the sleeve and the driven member; and an introducing passage through which gas can be introduced into the gas chamber, and can be configured to push the driven member in response to a pressure of the gas introduced into the gas chamber.

With such a configuration, the driven member can be pushed to the other side in the longitudinal direction of the sleeve by introducing the air into the gas chamber. In this case, for example, a compressor provided as part of hospital equipment can be used as the air supply source.

Further, by using a feature of introducing the air, as in the above-described configuration, it is possible to increase the extension-contraction range of the driven member with respect to a case where a biasing member such as a coil spring is used.

In other words, in a case where a biasing member is used, the extension-contraction stroke of the driven member is restricted by a minimum size of the biasing member in a contracted state and a biasing member size serving to obtain the minimum necessary biasing force, whereas in the case of a configuration in which gas is introduced, such restrictions are eliminated and a large extension-contraction range of the driven member can be designed.

Further, when a biasing member is used, only a biasing force that has been designed therefor has to be used as the pushing force of the driven member, whereas in a case where gas is used, the pushing force of the driven member can be adjusted by adjusting the gas pressure.

In accordance with the present invention, it is possible to provide a compact and lightweight manipulator device that occupies small area during operation. Further, by contrast with a manipulator device using an electrically driven actuator or electric motor, this manipulator device can be manufactured at a lower cost, there is no risk of failure caused by current leakage or disconnection, reliability is high, and cleanliness is good.

The invention claimed is:

1. A medical manipulator device that displaceably holds a medical instrument, comprising:
   a stage section that can hold the medical instrument;
   a plurality of actuators each having first and second ends spaced apart longitudinally, the first end of each of the actuators being linked to the stage section;
   a base section linked to the second end of each of the plurality of actuators; and
   an introducing chamber provided in each of the actuators and into which a liquid can be introduced, wherein
   each of the actuators causes the medical instrument and the stage section to displace with respect to the base section by extending or contracting in the longitudinal direction of the actuator in response to a pressure of the liquid inside the introducing chamber, and wherein at least one of the actuators is provided with:
   a cylindrical sleeve;
   a driven member provided slidably within the sleeve so that the introducing chamber is between the sleeve and the driven member, the driven member maintaining a sealed state with respect to the liquid and being displaceable relative to the sleeve along a first longitudinal direction in response to a pressure applied to the liquid; and
   a pushing section that can push the driven member in a second longitudinal direction opposite the first longitudinal direction so that the pushing section displaces the driven member in the second longitudinal direction when the pressure of the liquid is reduced.

2. The medical manipulator device according to claim 1, wherein the stage section is configured to be capable of magnetically holding the medical instrument via a permanent magnet provided at either or both of the stage section and medical instrument.

3. The medical manipulator device according to claim 1, wherein
at least one of the actuators is
magnetically and detachably linked to the stage section via a stage-side permanent magnet provided at either or both of first end of the actuator and the stage section, and
magnetically and detachably linked to the base section via a base-side permanent magnet provided at either or both of the second end of the at least one actuator and the base section.

4. The medical manipulator device according to claim 3, wherein
a spherical shaft formed by a permanent magnet or a magnetic body is provided at one of the actuator and the stage section, and a spherical bearing that is formed by a permanent magnet or a magnetic body and that can be magnetically linked to the spherical shaft is provided at the other of the actuator and the stage section,
a spherical shaft formed by a permanent magnet or a magnetic body is provided at one of the actuator and the base section, and a spherical bearing that is formed by a permanent magnet or a magnetic body and that can be magnetically linked to the spherical shaft is provided at the other of the actuator and the base section, and
the spherical shafts and spherical bearings are magnetically and detachably matched so that the actuator, the stage section and base section are angularly adjustably linked.

5. The medical manipulator device according to claim 1, wherein the pushing section is formed by a biasing section for applying a biasing force between the sleeve and the driven member.

6. The medical manipulator device according to claim 1, wherein the pushing section comprises a gas chamber that is formed between the sleeve and the driven member, and an introducing passage through which gas can be introduced into the gas chamber, and the pushing section is configured so that the driven member is pushed in response to a pressure of the gas introduced into the gas chamber.

7. The medical manipulator device according to claim 1, wherein
the driven member of the actuator is provided with a seal mechanism formed by an elastic body in a sliding section between the inner wall of the sleeve and the driven member,
the seal mechanism conducts sealing in a state in which the pressure of the liquid inside the sleeve can be released by causing the liquid to leak to the open side of the sleeve from a storage section in a state in which an excess load acts upon the actuator, and
the sleeve has an accumulation section in which the leaked liquid can be accumulated inside the sleeve.

8. The medical manipulator device according to claim 1, wherein
the actuator is further provided with:
a liquid inlet/outlet port that communicates with the introducing chamber; and
a tube that is connected at one end to the liquid inlet/outlet port and connected at the other end to a pressurized liquid supply port through which the liquid can be supplied, and wherein the pressurized liquid supply port and the tube are connected so that an excess load acts upon the actuator causes the liquid to leak from the connection site of the pressurized liquid supply port and the tube before the leaks in connection of the liquid inlet/outlet port and the tube.

9. The medical manipulator device according to claim 1, wherein the actuator is provided with a coating section formed by a flexible film that covers an outer surface of the sleeve.

10. The medical manipulator device according to claim 1, wherein the liquid includes either water or silicone oil as a main component.

11. The medical manipulator device according to claim 1, wherein the plurality of actuators together with the base section and stage section constitute a Stewart-Gough mechanism.

12. The medical manipulator device according to claim 1, wherein the medical instrument is an endoscope.

13. The medical manipulator device according to claim 12, wherein the medical instrument is an endoscope such as a laparoscope for conducting observations in an abdominal cavity or a thoracoscope for conducting observations in a thoracic cavity.

14. The medical manipulator device according to claim 1, wherein the base section is configured to be linkable to a multi-degree-of-freedom grasping arm with flexibility that is provided so as to extend from a fixing member that is fixed to a patient.

15. The medical manipulator device according to claim 14, wherein the fixing member is a belt for attaching the medical manipulator device in the vicinity of a pelvis of hypogastrium of the patient.

16. The medical manipulator device according to claim 1, wherein
the medical instrument is an endoscope including a distal end to be inserted into a body of a patient,
the driven member can be displaced in a direction for contracting the actuator along the longitudinal direction in response to the pressure of the liquid inside the introducing chamber,
the pushing section can push the driven member in a direction for extending the actuator along the longitudinal direction in a state in which the pressure of the liquid is reduced, and
the stage section can hold the endoscope in a state in which the endoscope penetrates through the base section in such a manner that the distal end of the endoscope is disposed opposite to the stage section with respect to the base section.

17. An actuator for use in a medical manipulator device that holds a medical instrument and comprises a base section, and a stage section that can hold the medical instrument,
the actuator having first and second ends spaced apart longitudinally and comprising:
a first linking section provided at the first end of the actuator and can be linked to the stage section;
a second linking section provided at the second end of the actuator and can be linked to the base section;
a cylindrical sleeve;
an introducing chamber in the sleeve and into which a liquid can be introduced;
a driven member provided slidably within the sleeve so that the introducing chamber is between the sleeve and the driven member, the driven member maintaining a sealed state with respect to the liquid and being displaceable in a first longitudinal direction in response to a pressure applied to the liquid; and a pushing section that can push the driven member in a second longitudinal direction opposite the first longitudinal direction, wherein the actuator extends or contracts in response to a pressure of the liquid introduced into the introducing chamber, so that the first linking section and the second linking section approach or separate from each other, and wherein the pushing section displaces the driven member in the second longitudinal direction when the pressure of the liquid is reduced.

18. The actuator according to claim 17, further comprising:
a liquid inlet/outlet port that communicates with the introducing chamber; wherein
the first linking section is provided at one of the sleeve and the driven member, and the second linking section is provided at the other of the sleeve and the driven member.

19. The actuator according to claim 17, wherein
the stage section includes a first magnetic section,
the base section includes a second magnetic section,
the first linking section and the second linking section include magnetic bodies, and
the first magnetic section and the first linking section, and the second magnetic section and the second linking section are magnetically and detachably linked, respectively.

20. The actuator according to claim 17, wherein the pushing section includes a biasing section for applying a biasing force between the sleeve and the driven member.

21. The actuator according to claim 17, wherein the pushing section is provided with:
a gas chamber that is formed between the sleeve and the driven member; and
an introducing passage through which gas can be introduced into the gas chamber, and
the pushing section pushes the driven member in response to a pressure of the gas introduced into the gas chamber.

22. The actuator according to claim 17, wherein
the medical instrument is an endoscope including a distal end to be inserted into a body of a patient,
the driven member can be displaced in a direction for contracting the actuator along the longitudinal direction in response to the pressure of the liquid inside the introducing chamber,
the pushing section can push the driven member in a direction for extending the actuator along the longitudinal direction in a state in which the pressure of the liquid is reduced, and
the stage section can hold the endoscope in a state in which the endoscope penetrates through the base section in such a manner that the distal end of the endoscope is disposed opposite to the stage section with respect to the base section.

* * * * *